United States Patent
Thomas

(10) Patent No.: US 9,726,640 B2
(45) Date of Patent: Aug. 8, 2017

(54) CIRCUIT AND METHOD OF PROVIDING A STABLE DISPLAY FOR EDDY CURRENT INSTRUMENTS

(71) Applicant: Andrew Thomas, Westford, MA (US)

(72) Inventor: Andrew Thomas, Westford, MA (US)

(73) Assignee: OLYMPUS SCIENTIFIC SOLUTIONS AMERICAS INC., Waltham, MA (US)

( * ) Notice: Subject to any disclaimer, the term of this patent is extended or adjusted under 35 U.S.C. 154(b) by 286 days.

(21) Appl. No.: 14/550,217

(22) Filed: Nov. 21, 2014

(65) Prior Publication Data

US 2016/0146759 A1 May 26, 2016

(51) Int. Cl.
*G01N 27/90* (2006.01)

(52) U.S. Cl.
CPC ....... *G01N 27/9046* (2013.01); *G01N 27/908* (2013.01)

(58) Field of Classification Search
CPC ........ H04B 1/707; H04B 2201/709709; H04B 1/1027; H04B 1/7087; H04B 10/548; H04B 1/7183; H04B 1/662; H04J 3/0638; H04J 3/0602; G01R 27/28; G01R 23/163; G01R 25/00; G01R 27/06; G01R 27/32; G01N 27/9046; G01N 27/904; G01N 27/908

See application file for complete search history.

(56) References Cited

U.S. PATENT DOCUMENTS

| | | | | |
|---|---|---|---|---|
| 5,184,071 | A * | 2/1993 | Tasca | G01N 27/904 324/232 |
| 6,734,669 | B2 * | 5/2004 | Lopez | G01N 27/9046 324/238 |
| 6,798,197 | B2 * | 9/2004 | Lopez | G01N 27/9046 324/238 |
| 2003/0227288 | A1 * | 12/2003 | Lopez | G01N 27/9046 324/255 |
| 2004/0066189 | A1 * | 4/2004 | Lopez | G01N 27/9046 324/238 |
| 2015/0256909 | A1 * | 9/2015 | Kappus | H04R 3/00 381/120 |

* cited by examiner

*Primary Examiner* — Alesa Allgood
(74) *Attorney, Agent, or Firm* — C. Tricia Liu

(57) ABSTRACT

A rotary bolt hole eddy current inspection scanner using a differential eddy current probe, the circuitry of the scanner is embodied with a filtering circuit with three filters: FIR (Finite Impulse Response), a low pass filter, and a phase control filter (by means of a Hilbert transform). The result from a scan of a bolt hole is an output signal on an impedance plane exhibiting a "backwards 6" shape of stable size when the scanner changes its rotating rate significantly.

16 Claims, 4 Drawing Sheets

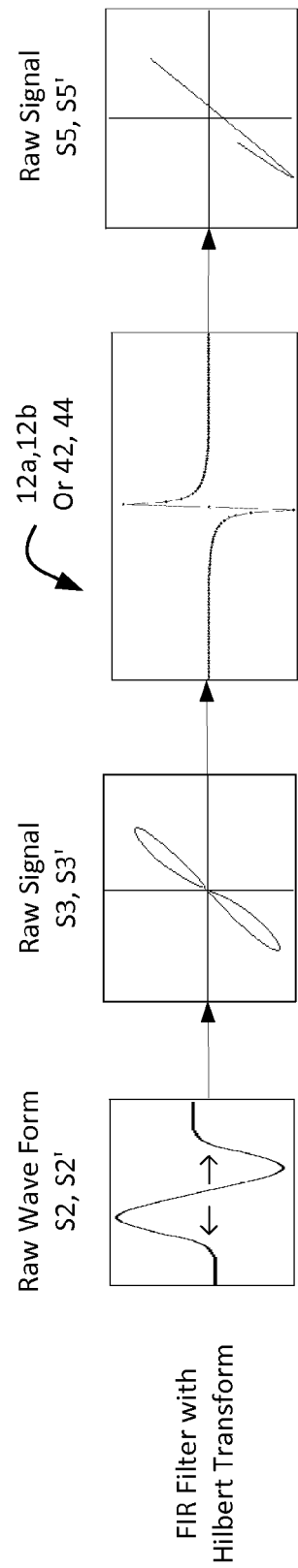

CIRCUIT AND METHOD OF PROVIDING A STABLE DISPLAY FOR EDDY CURRENT INSTRUMENTS

FIELD OF THE INVENTION

This invention relates to non-destructive testing and inspection (NDT/NDI), particularly to an improved signal processing circuitry of an eddy current inspection instrument with a rotary scanner implementation to achieve a stable display in a testing result.

BACKGROUND OF THE INVENTION

An eddy current probe uses an alternating current that flows through a wire coil and generates an oscillating magnetic field. If the probe and its magnetic field are brought close to a conductive material like a metal test piece, a circular flow of electrons known as an eddy current moves through the metal and generates its own magnetic field, which interacts with the coil and its field through mutual inductance.

Changes in metal thickness or defects like near-surface cracking interrupt or alter the amplitude and pattern of the eddy current and the resulting magnetic field. This in turn affects the movement of electrons in the coil by varying the electrical impedance of the coil. The eddy current instrument plots changes in the impedance amplitude and phase angle, which can be used by a trained operator to identify changes in the test piece.

One use of eddy current instruments is to examine cracking inside bolt holes, often with automated rotary scanners. The signals returned from the probe are displayed using an impedance plane plot that graphs coil resistance on the x-axis and inductive reactance on the y-axis. Variations in the plot correspond to variations in the test piece.

Conventionally the rotary scanners employ a "dual probe" or differential eddy current probe to scan the interior of the bolt holes. When the differential probe (two probes) passes a crack or a few cracks, the direct response of the differential probe shows on the display as a figure "8", with the knot of the two circles representing the moment when the crack is right between the two coil sensors. The signals from a probe inserted into a test block with a standard crack flaw typically produce displays on an impedance plane as a "figure 8". When using the instrument configured in this way, the analyst may accidentally pass over some flaws because they produce a display pattern very similar to the standard crack "figure 8" but flipped over in such a way that they appear very similar.

In calibrating the eddy current rotary scanner, it is a long known practice that eddy current field engineers look for "backwards 6" figures on the impedance plane display as an indication of a standard indication (the standard crack) or default status of the tube or bolt hole inspections. This calibration set up is often a preferred alternative to the "figure 8" as a standard indication display. When an abnormality exists, such as a crack or corrosion, the "backwards 6" changes in shape or direction to some degree. Although the raw detected signal response is presented as a "figure 8", it is not desirable, since the abnormality often shows in the first region of the coordinate and the "figure 8" confuses the viewing of the abnormality. In existing practice, an Infinite Impulse Response (IIR) filter is used to shift the phase of frequency response for signals lower that certain frequency.

One problem with this type of prior art design is that it causes inspectors in the field to have to deal with a "backwards 6" drastically changing in size, or changing into a "figure 8" when the revolutions per minute (RPM) speed of the rotary scanner changes. When the frequency decreases, the size of the "backwards 6" becomes smaller; when the frequency increases, the size of the "backwards 6" becomes bigger; and when the frequency increases beyond the range of the IIR filter, the "figure 8" displays.

Considering the background information above, a solution that by design provides a steady display of an eddy current inspection result without the need to readjust the amplitude and frequency settings of the instrument would be of great economic value. Rotary scanner such as those for bolt hole inspections would take place in less time and with more effectiveness. The task of the inspection would be visually much more pleasant to handle.

SUMMARY OF THE INVENTION

It is a general object of the present disclosure to provide a signal processing and plotting method that yields a controlled and systematic display of the response of an eddy current differential probe inspecting the interior of a cylindrical cavity.

It is further an object of the present disclosure to control phase independently from low and high pass filter parameters. One implementation is to use a Hilbert transform with which a 90 degree phase shift is intrinsic and definitive, and an inspector can easily switch from an ideal differential probe signal to a phase-shifted differential signal. Once optimized for application, high and low pass filter frequency settings can be linked to the RPM setting of the rotary bolt scanner to provide a reasonable variation range due to probe friction in the hole, while maintaining a largely constant displayed signal size.

It is further another object of the present disclosure to use a Hilbert transform to phase shift the signals at the "flat" range of frequency response of a high pass filter, so that motor speed variation does not cause an erratic signal amplitude (and thus image size) while displaying the phase-shifted variant of the probe signal.

The preferred embodiment of the disclosure uses three Finite Impulse Response (FIR) filters: low pass, high pass, and phase control (by means of a Hilbert transform). Coefficients of the FIR filters are calculated and loaded in real time, where ideal differential and phase shifted responses can be achieved. Phase control is simplified by using a FIR Hilbert transform that automatically provides a 90 degree phase shift to all the frequencies in the pass band set by the low pass and high pass filters. The advantage of using the FIR Hilbert transform approach is attributed to its phase change regardless of frequency. As a result, filter parameters can be established between the high and low pass filter settings and the scanner motor speed setting. When the inspector changes the rotary scanner speed, the filters can also be automatically reconfigured to frequencies that provide the same inspection at the new probe rotation rate. All settings produce the same signal amplitude and image size.

BRIEF DESCRIPTION OF THE DRAWINGS

FIG. 3 is a schematic view of stages of the waveforms from raw detected signals to processed signals using the circuitry according to the present disclosure.

DETAILED DESCRIPTION OF THE INVENTION

It should be noted that all functions herein described as a digital circuit can also be implemented using analog circuits. An analog method has been practical for many years, and is not an improvement made possible only by digital methods, and should fall under the scope of the present disclosure. It should also be noted that the core concept of this patent is the inclusion of a wide frequency range phase shift filter. The use of a Hilbert transform can be directly implemented as shown in present disclosure, or it can be done indirectly by the use of other frequency sensitive circuits used together to make a composite filter.

Figure 1:
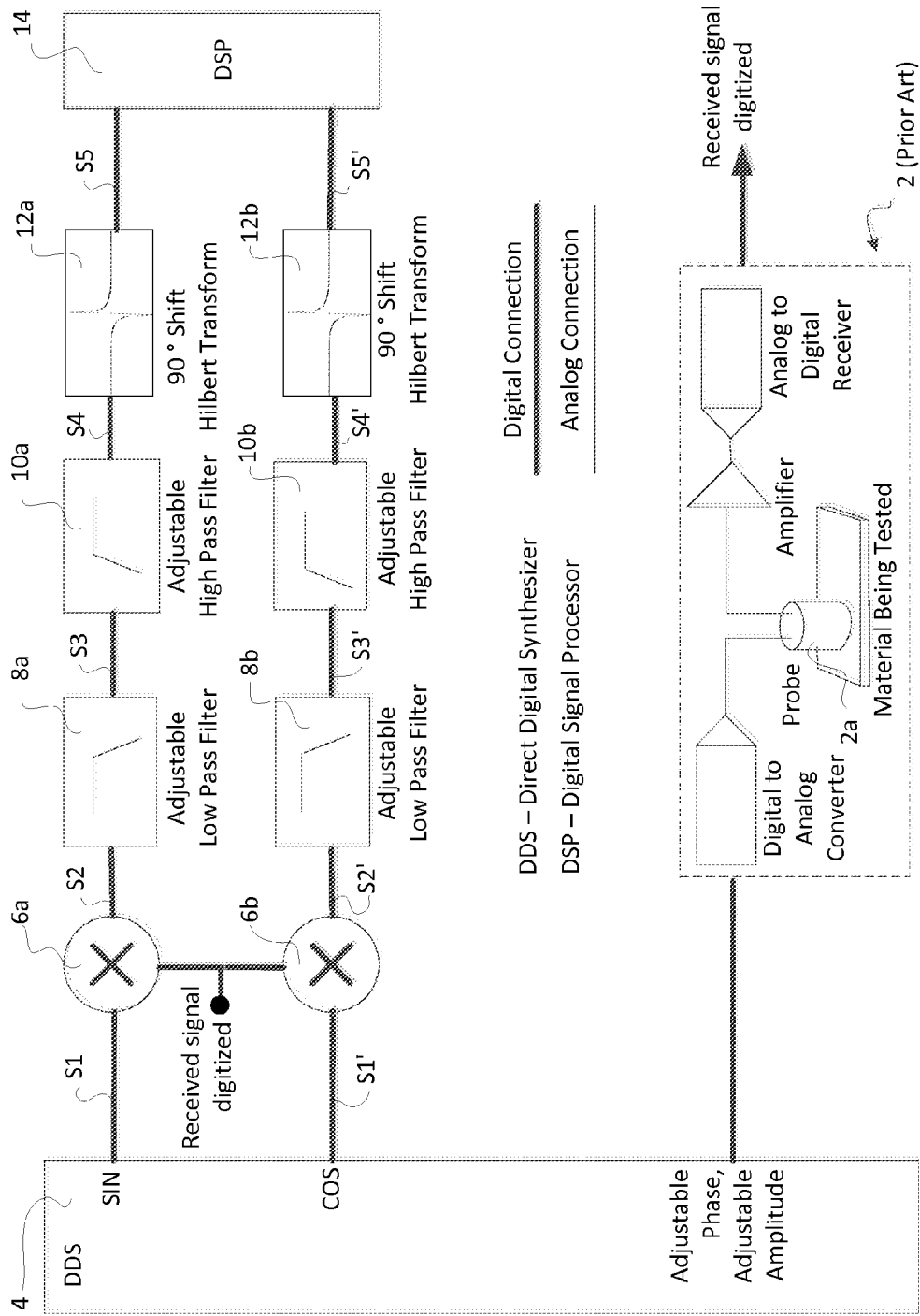
FIG. 1 is a schematic view of the signal processing circuitry according to one embodiment of the present disclosure.

Referring to FIG. 1, an exemplary embodiment of the an eddy current front end circuitry 2 is used to digitize signal coming back from probe 2a which is attached to a rotary bolt hole scanner (not shown). The digitized signal is provided by circuitry 2.

The circuitry of the present disclosure comprises the front-end circuitry 2, a direct digital synthesizer (DDS) 4, a synchronous detector 6a for sine waves, a synchronous detector 6b for cosine waves, an adjustable low pass filter 8a for sine waves, an adjustable low pass filter 8b for cosine waves, an adjustable high pass filter 10a for sine waves, an adjustable high pass filter 10b for cosine waves, a first Hilbert transform filter 12a for sine waves, a second Hilbert transform filter 12b for cosine waves, and a digital signal processor 14.

DDS 4, synchronous detectors 6a and 6b, adjustable low pass filters 8a and 8b, adjustable high pass filters 10a and 10b, Hilbert transform filters 12a and 12b, and digital signal processor 14 are herein collectively called a digital signal processing circuit. It should be noted that signals downstream the digitized signals are called response signals, whereas there are other specific terms for each stage of the response signals, such as raw detected signals S3 and S3'.

Continuing to refer to FIG. 1, direct digital synthesizer 4 generates three kinds of signals: a reference sine wave S1, a reference cosine wave S1', and a transmit sine wave. The transmit sine wave is fed to front-end circuitry 2 with an adjustable phase and adjustable amplitude. The digitized signal is sent to synchronous detectors 6a and 6b respectively. Synchronous detector 6a separates and produces the real component of digitized signal S2. Synchronous detector 6b detects the imaginary component of digitized signal S2'.

Detected real component signal S2 and detected imaginary component signal S2' are filtered by adjustable low pass filter 8a and adjustable low pass filter 8b respectively to remove unwanted sine waves. Adjustable low pass filter 8a removes unwanted sine waves in detected real component signal S2 so that a raw detected signal of real component S3 contains only the amplitude which is the real component. Adjustable low pass filter 8b removes unwanted cosine waves in detected imaginary component signal S2' so that a raw detected signal of imaginary component S3' contains only the amplitude which is the imaginary component. "Raw detected signal" is herein referred to as a response signal to be further filtered by high pass filters described below.

Raw detected signals of real component S3 and imaginary component S3' pass through adjustable high pass filter 10a and adjustable high pass filter 10b respectively to eliminate all frequencies below a selected frequency. The result is a bandpass filtered signal of real component S4 and a bandpass filtered signal of imaginary component S4'. The selected frequency is conventionally determined by the rotation rate of the scanner so that the display of the inspection result is readable.

Still referring to FIG. 1, it should be understood that synchronous detector 6a, adjustable low pass filter 8a, and adjustable high pass filter 10a are all conventional to eddy current instruments. Signal S1 and S1' are conventionally in the shape of a "figure 8". Bandpass filtered signals S4 and S4' are conventionally in a shape of a "backwards 6" which represents the inspection results. One of the issues with the bandpass filtered signals S4 and S4' is that when the rotation rate of scanner is changing, the size of the "backwards 6" on the display changes drastically, which has been problematic for field inspectors. Details of the above signal display related to the "figure 8" and the "backwards 6" are explained in association with FIGS. 2a and 2b.

One of the novel aspects of the present disclosure is to employ Hilbert transform filter 12a in combination of high pass filter Hilbert transform filter 12a to digital signal processor 14. Direct digital synthesizer 4 also detects cosine waves from synchronous detector 6b, and sends the cosine waves of the rotary bolt scanner's signals through an adjustable low pass filter 8b, an adjustable high pass filter 10b, and a Hilbert transform filter 12b, to digital signal processor 14.

Bandpass signal of real component S4 and bandpass signal of imaginary component S4' pass through a 90 degree shift in Hilbert transform filter 12a and a 90 degree shift in Hilbert transform filter 12b respectively, where the signals are adjusted for phase (independently of amplitude), and sent to digital signal processor 14 as a bandpass phase-adjusted signal of real component S5 and a bandpass phase-adjusted signal of imaginary component S5'.

Figure 2A:
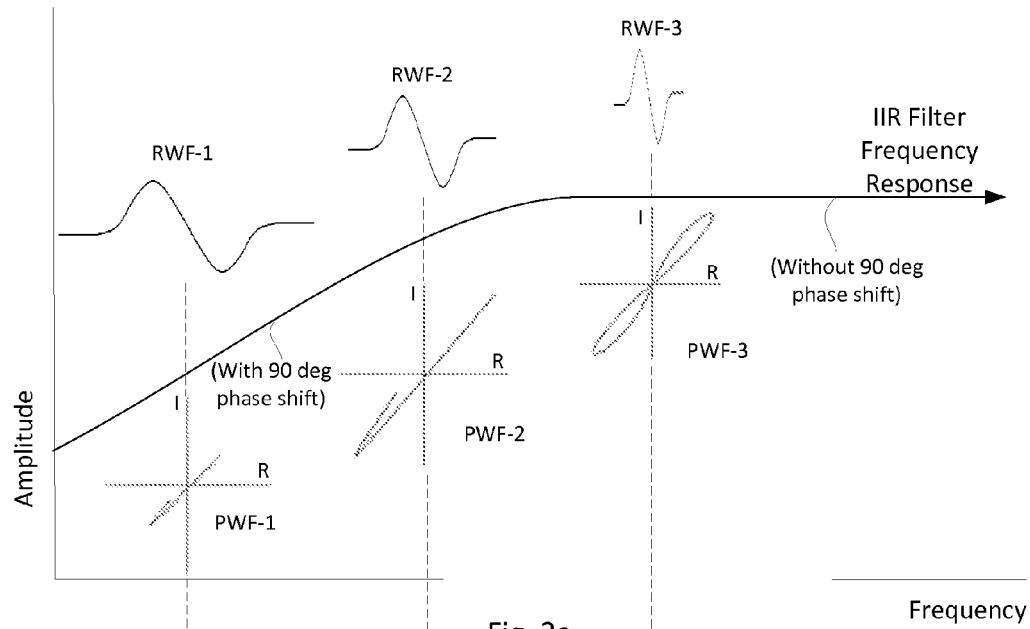
FIG. 2a is a schematic view of raw and processed waveforms processed by prior art circuitry, using IIR for phase shift.

Reference is now made to FIG. 2a, which shows the processing of a series of phase-adjusted sine waves of different frequency in a prior art practice. In the large coordinate shown in FIG. 2a, the x-axis is the frequency; the y-axis is the amplitude of the signals. The "frequency response" curve stretches from the lower left corner to the upper right corner of the coordinate, representing the "amplitude response" of the prior art IIR high pass filter in response to changes in response signals' frequency. The changes in response signals' frequencies are largely caused by the change in scanning speed of the probe, such as RPM speed.

Raw waveforms RWF-1, RWF-2 and RWF-3 are the response signals after each being filtered by low pass filters 8a and 8b. They are different in frequencies when the rotary scanner changes rotating speed in revolutions per minute (RPM). Existing arts use an infinite Impulse Response filter (IIR) to adjust raw detected signal phase 90 degrees. After been processed by the IIR high pass filter, raw waveforms below the turning point on curve of "frequency response of the high pass filter" has a 90 degree of phase shift (RWF-1 and RWF-2), whereas the raw waveforms above the turning point, such as RWF-3, is in 0 degree phase. The complex signals after passing high pass filters 10a and 10b present in forms of PWF-1, PWF-2, and PWF-3. It should be noted that the x-axis of PWF-1, PWF-2, and PWF-3 refers to the real, or 'R', components of the response signals. The y-axis refers to the imaginary, or 'I', components of the response signals. In another word, PWF-1, PWF-2, and PWF-3 are displays in impedance planes. As can be seen, PWF-1, -2 and -3 are in the shapes of sometimes a "backwards 6" or sometimes a "figure 8", and their sizes change in impedance planes.

It is a long known practice that eddy current engineers look for "backwards 6" figures on the display showing a standard indication during calibration for tube inspections. When an abnormality exists during inspection, such as a crack or corrosion, the "backwards 6" changes shape. A "figure 8" display is not desirable, since the abnormality often shows in the first region of the coordinate, and the "figure 8" confuses the viewing of the abnormality. The problem of prior art design is that it causes inspectors in the field to have to deal with a "backwards 6" that drastically changes in size, or changes into a "figure 8" when the rotary scanner's RPM speed changes. When the frequency decreases, the size of the "backwards 6" becomes smaller; when the frequency increases, the size of the "backwards 6" becomes bigger; and when the frequency increases beyond the range of the IIR filter, the "figure 8" displays.

It should be particularly noted that the 90 degree phase shift mentioned above is not a limitation to the present disclosure. A phase shift in a range of 70~110 degrees, as long as it serves the purpose of flipping the display in the impedance plane from a "figure 8" to a "backwards 6", can be used in the framework of the present disclosure.

Figure 2B:
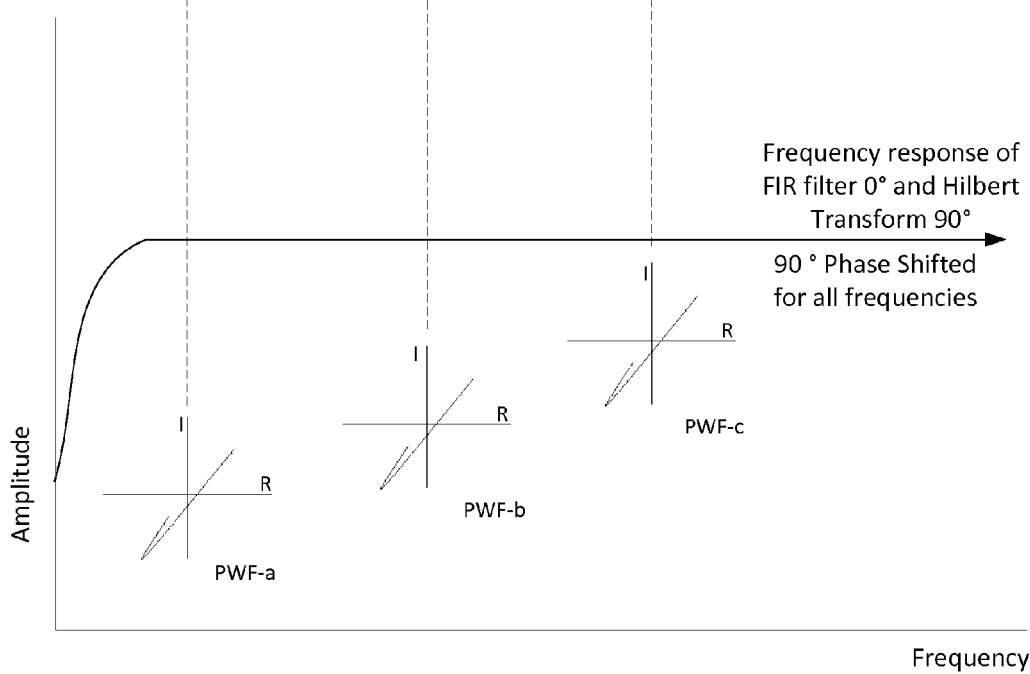
FIG. 2b is a schematic view of raw and processed waveforms processed by the processing circuitry with an FIR and Hilbert transform, according to the present disclosure.

Reference is now made to FIG. 2b, which shows an important novel aspect of the present disclosure to negate the problem of drastically changing "backward 6" on the display screen. In FIG. 2b, the x-axis is also the frequency of the high pass filters, and the y-axis is the amplitude of the response signals. The high pass filters (10a & 12a) "frequency response curve" is presented as flat versus that of a curve in FIG. 2a. This is because the range of response signals' frequencies is in the range at which filters respond with constant amplitude.

Referring to FIG. 2b and FIG. 1, the signal processing circuit in the present disclosure uses FIR (Finite Impulse Response) adjustable high pass filters 10a and 10b, instead of the IIR used by prior art in FIG. 2a. As shown by the frequency response curve in FIG. 2a, FIR filters 10a and 10b maintain constant phase with the 90 degree phase change, and do not change phase. However, without changing phase the default processed signal display from the FIR filters would be presented as a "figure 8". In order to achieve the "backwards 6" figure as required by the convention of the eddy current inspection, Hilbert transform filters 12a and 12b are used, which shift the phase 90 degrees on the flat part of the frequency response curve. As shown in FIG. 2b, the same raw detected signals RWF-1, RWF-2 and RWF-3, after being processed by FIR filters 10a and 10b and Hilbert transform filters 12a and 12b, become processed waveforms in "backwards 6" with the same sizes as in PWF-a, PWF-b and PWF-c shown in respective impedance planes. It should be noted that the x-axis of PWF-a, PWF-b, and PWF-c refers to the real, or 'R', components of the response signals. The y-axis refers to the imaginary, or 'I', components of the response signals. This is attributed to the nature of the Hilbert transform that performs the 90 degree phase shift when the amplitude remains constant while the frequency changes.

When the phase of reference sine wave S1 and reference cosine wave S1' (the "figure 8") is adjusted 90 degrees by using the Hilbert transform filters 12a and 12b, the three exemplary raw signal waveforms in FIG. 2a do not vary the sizes of the sine waves (the "backwards 6") in display for PWF-a, PWF-b and PWF-c. This is because the phase change is conducted at the range where frequency response is substantially constant.

One skilled in the art should appreciate that alternatively an eddy current instrument can be configured to have two signal processing designs working in parallel in one instrument, one with the prior art design as shown in FIG. 2a, and one with the novel design as shown in FIG. 2b. Inspectors can then have a choice, depending their preference, to choose either the "figure 8" display mode, or the improved "backwards 6" display mode.

Referring to FIG. 3, a schematic diagram shows signals at different stages of the signal processing done by the digital signal processing circuit from synchronous detector 6a to Hilbert transform filter 12a (or synchronous detector 6b to Hilbert transform filter 12b) in FIG. 1. As shown in FIG. 3, raw sine waveform (S2, S2') is processed to raw signal (S4, S4') in a "figure 8" by adjustable low pass filter 8a and adjustable high pass filter 10a (or adjustable low pass filter 8b and adjustable high pass filter 10b). Then signal (S4, S4') in the "figure 8" is transformed to a "backwards 6" in display signal (S5, S5') by Hilbert transform filter 12a or 12b.

Figure 4:
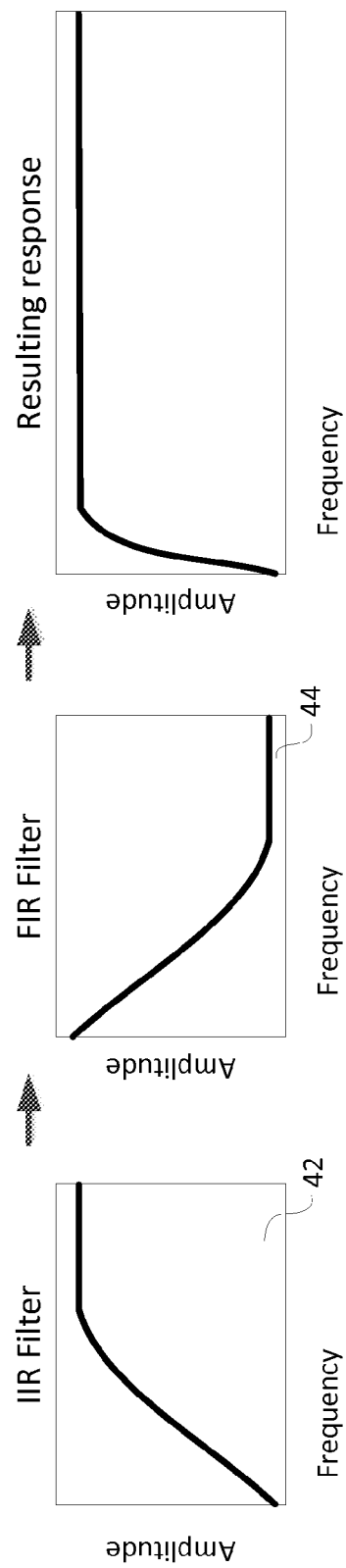
FIG. 4 is an alternative signal processing circuitry method achieving the same purpose as that shown in FIG. 3.

Reference is now made to FIG. 4. One skilled in the art should also note that using a FIR adjustable high pass filter 10a and a Hilbert transform filter 12a is not the only way of achieving the frequency response shown in FIG. 2b. An IIR filter having a frequency response 42 and a FIR filter have a frequency response 44 also achieve the purpose of having a frequency response 46. The purpose here is to achieve a phase change of 90 degrees for frequencies within a range wherein the frequency response (amplitude) is "flat," or substantially constant.

Although the present invention has been described in relation to particular exemplary embodiments thereof, many other variations and modifications and other uses will become apparent to those skilled in the art. It is preferred, therefore, that the present invention not be limited by the specific disclosure. For example, the scope of the present disclosure may be applied to other differential probes producing continuous energy waves, such as, but not limited to, ultrasonic differential continuous probes.

What is claimed is:
1. A circuitry for an eddy current inspection instrument configured to conduct eddy current inspection of abnormality of a test object, the instrument is coupled to an eddy current probe moving at a scanning speed varying in a speed range during the inspection, the circuitry comprises,
   a front-end circuit for energizing the probe, receiving eddy current response, digitizing and converting the response to response signals with a range of response frequencies related to the scanning speed,
   a digital processing circuit configured to process the response signals for displaying inspection result, the processing circuit further comprising a filtering circuit configured to filter the response signals from raw detected signals to processed signals, and to apply a phase change of the raw detected signals in a vicinity of 90 degrees while the filtering circuit maintains a substantially constant frequency response within the range of response frequencies, and,
   wherein the digital processing circuit further comprises a direct digital synthesizer, generating a real component of a reference signal and an imaginary component of the reference signal, a first synchronous detector configured to detect the real component of the reference signal, and a second synchronous detector configured to detect the imaginary component of the reference signal.

2. The circuitry of claim 1, wherein the frequency response is an amplitude response of the filtering circuit in response to change in frequencies of the response signals.

3. The circuitry of claim 1, wherein the vicinity of 90 degree is in a range of 70~110 degrees.

4. The circuitry of claim 1, wherein the response signals coming out of the front end circuit are fed to the first detector and the second synchronous detector, generating the corresponding raw detected signals.

5. The circuitry of claim 4, wherein the real component of the reference signal is in a form of sine waves and the imaginary component of the reference signal is in a form of cosine waves.

6. The circuitry of claim 4, wherein the filtering circuit further comprises a low pass filter filtering the digitized signals.

7. The circuitry of claim 1, wherein the probe is a differential probe which is devised on a rotary scanner configure to make circular or helical scan on a surface of the test object.

8. The circuitry of claim 7, wherein the test object is a standard calibration piece having a shape of a hole or tube, the calibration piece having a standard indication with a known indication size and direction, the scanner traverses the surface of the test object with a range of rotary speed (RPM).

9. The circuitry of claim 8, wherein the filtering circuit further comprises a infinite impulse response high pass filter and a finite impulse filter configured to provide signal with a substantially constant amplitude over the range of the response frequency make a 90 degree phase change for the signals.

10. The circuitry of claim 9, wherein the infinite impulse response high pass filter and the finite impulse response high pass filter produces processed signals shown on an impedance plane that substantially in a shape of the "backwards 6".

11. The circuitry of claim 10, wherein the infinite impulse response high pass filter and the finite impulse response high pass filter are configured so that size of the "backwards 6" shown on the impedance plane is substantially constant when the scanner traverses test object surface with the range of rotary speed.

12. The circuitry of claim 8, wherein the filtering circuit further comprises a finite impulse response high pass filter providing signal with a substantially constant amplitude over the range of the response signal frequencies and a Hilbert transform high pass filter providing phase change in a vicinity of 90 degrees for the signals.

13. The circuitry of claim 12, wherein the finite impulse response high pass filter producing processed signals shown on an impedance plane is substantially in a shape of a "figure 8".

14. The circuitry of claim 13, wherein the finite impulse filter and the Hilbert transform filter producing processed signals shown in an impedance plane substantially as the shape of a "backwards 6".

15. The circuitry of claim 14, wherein the filtering circuit is configured so that size of the "backwards 6" shown on the impedance plane is substantially constant when the scanner traverses the surface with the range of rotary speed.

16. The circuitry of claim 15 further includes a display having a mode change allowing selection between a mode for displaying the "figure 8" and a mode for displaying the "backwards 6".

* * * * *